United States Patent
Van Deripe (12)

(10) Patent No.: US 6,358,194 B1
(45) Date of Patent: Mar. 19, 2002

(54) MEDICAL USE OF XENON-133 IN RADIATION THERAPY OF CANCER

(76) Inventor: Donald Ray Van Deripe, 1534 Woodbury Dr., St. Charles, MO (US) 63304

( * ) Notice: Subject to any disclaimer, the term of this patent is extended or adjusted under 35 U.S.C. 154(b) by 0 days.

(21) Appl. No.: 09/563,759

(22) Filed: May 1, 2000

(51) Int. Cl.$^7$ ............................. A61M 3/00; A61N 5/00
(52) U.S. Cl. .......................................................... 600/4
(58) Field of Search ........................ 600/1–8; 424/1.65, 424/9.322, 1.11, 1.69, 1.41, 450; 534/10, 11

(56) References Cited

U.S. PATENT DOCUMENTS

| | | | | |
|---|---|---|---|---|
| 3,848,773 A | * | 11/1974 | Adler et al. ................. | 600/3 |
| 6,159,141 A | * | 12/2000 | Apple et al. ................. | 600/3 |
| 6,162,165 A | * | 12/2000 | Apple et al. ................. | 600/3 |
| 6,251,059 B1 | * | 6/2001 | Apple et al. ................. | 600/3 |

OTHER PUBLICATIONS

VanDeripe, Donald R., Gas Microbubbles in Biology: Their Relevance in Histology, Toxicology, Physiology and Anesthesia, 2001, Taylor & Francis, Toxicology Methods, 11:107–126.*

* cited by examiner

*Primary Examiner*—Kevin Shaver
*Assistant Examiner*—Brian Szmal

(57) ABSTRACT

The disclosure details a novel method of use of the radioactive isotope Xenon-133 (Xe-133) in the radiotherapy of cancer. Xe-133 gas is infused directly into the core of the tumor and diffuses as microbubbles of gas toward the tumor boundaries where it is eventually taken up into patent capillaries and excreted by the lungs. During its infusion and diffusion throughout the tumor the Xe-133 exposes the cancerous tissue to very high fluxes of beta rays which penetrate tissue at about one millimeter increments. This limited penetration is very distructive to tissue while the Xe-133 gas is contained within the tumor. However, when the Xe-133 reaches the surface of the tumor, normal capillary blood flow carries it away and thereby minimizes exposure to normal tissues. Xenon-133 represents the only radioactive gas isotope which is suitable to practice the invention.

15 Claims, No Drawings

MEDICAL USE OF XENON-133 IN RADIATION THERAPY OF CANCER

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

The invention provides a novel means to apply radiation therapy to cancerous tumors not available in the prior art. Currently practiced radiation therapy is limited to two options, external beam X-ray therapy and surgical implantation of solid radioactive needles and rods (seeds). The new approach of this invention is to administer radiotherapy in the form of the radioactive gas Xenon-133, which is infused through a catheter directly into the core of the tumor. This method of radiation therapy allows for a major improvement in target to non-target radiation over external beam X-ray therapy. Also, the excretion of Xenon-133 gas by the lungs eliminates the need for surgical removal of the radiation source as is the case for implanted seeds.

BRIEF SUMMARY OF THE INVENTION

Current methods for radiotherapy of cancerous tumors are hampered by significant target to non-target dosimetry problems. External beam radiotherapy employs X-radiation which must be of sufficient energy to traverse non-diseased tissues prior to reaching the tumor, and most of the radiation then continues through the tumor to expose additional non-diseased tissue to unwanted irradiation. Since only a fraction of the incident radiations are absorbed by the tumor relative to normal tissues, the total radiation which can be administered is limited. An approach which has helped to some degree is multiple angle focusung of the X-ray beams, which improves the target to non-target safety about ten- to twentyfold.

Implantation of radioactive seeds, while more selective than external beam radiotherapy, still suffers from radiation spillover into normal tissue. In addition, seeds may migrate and they must be surgically removed when the radiation treatment is completed.

The method of the current invention involves the site selective infusion of a diffusible radioactive gas, Xenon-133 (Xe-133) into the core of the tumor. One might be tempted to question the usefulness of this approach, because the 0.346 MeV beta emissions from Xe-133 can penetrate tissue only to a depth of about one millimeter, which would restrict its utility to very small tumors. However, Xe-133 exhibits several desirable attributes which make it uniquely valuable when infused into a tumor. First, when infused into the core of the tumor, Xe-133 forms diffusible microbubbles of gas which can spread throughout the tumor [see Exhibit A]. Second, continuous infusion forces the spread of the gas as an expanding sphere completely filling the tumor with the radioactive Xe-133. Third, the Xe-133 gas, having spread to the periphery of the tumor, will be taken up into patent capillaries and carried away thereby protecting adjacent tissues from prolonged radiation exposure. Following its uptake into the capillary blood, Xe-133 will be carried to the lungs and excreted in the expired air. This uptake and excretion represents a safety feature unavialable from any other approach to radiotherapy. The enabling discovery by the inventor was the determination that Xenon exists in tissues as diffusible microbubbles of gas [Exhibit A].

DETAILED DESCRIPTION OF THE INVENTION

The disease of cancer is most often treated using three modalities alone or in combination, surgery, chemotherapy and radiation. Depending on type and location, tumors are treated by protocols developed from years of trial and error experience. Surgical excision, if practical, is usually the treatment of choice, often followed by chemotherapy and/or external beam radiation therapy. Although many chemotherapeutic combinations and regimens have been developed and remain in use, they generally suffer from lack of target to nontarget specificity with resulting toxicity to essential major organs such as the liver, kidneys and bone marrow. This often becomes the limiting factor in the effective treatment of the primary cancer and/or metastatic sites. External beam radiation, although effective in killing tumor tissue, also carries a major disadvantage in its relative lack of target to non-target specificity. Attempts to improve external beam x-ray beam therapy have included focused beams at varying angels which provides unitary improvement in tumor selectivity for each angle (radiation port) employed. This approach has been further enhanced by a device known as the Gamma Knife which can focus the x-ray beam over multiple angels providing a further improvement in target to non target irradiation. However, Gamma Knife instruments are quite expensive, not widely available and are generally limited to smaller tumors.

Attempts to improve the specificity and selectivity of tumor irradiation have focused on local deposition of radioactive elements (brachytherapy) which emit various types of radiations as they decay over time. Brachytherapy, using radioactive isotope doped rods or needles (seeds) implanted within the tumor, is a direct approach to radiotherapy, but it often contributes significant exposure to adjacent normal tissue. Brachytherapy can become further problematical in cases where these radioactive seeds migrate from their original implantation sites. Other disadvantages are the usual requirement for implanting a number of such seeds to provide comprehensive tumor site irradiation and that these seeds must be surgically removed when the therapy is completed.

Radiation is generally thought to kill cells by destroying the DNA contained in the cell nucleus. There are principally four types of radioactive decay which could effectively kill cells. These are auger electrons, alpha particles, beta particles and gamma rays. Auger electrons are impractical since they travel only micron distances in tissue and would therefore have to be localized within the cell nucleus to be effective, and no specific localization techniqes are available. Alpha particles travel distances of up to about one millimeter in tissue and are highly tissue-destructive radiations. However, they are generally long-life isotopes which, unless effectively and completely removed would irradiate tissues for years with consequent destruction of normal tissue and potential for radiation-induced cancer. There are no effective means available for the selective administration or removal of alpha-emitting isotopes. Radioisotopes best suited for local tumor tissue irradiation are those which emit beta particles (beta rays). The energy of these beta particle emissions are such that tissue penetration can range from about one millimeter up to 3 or 4 centimeters. Again, however, but with few exceptions, only direct introduction into the tumors provides a suitable means for their administration. In addition, those beta emmissions which travel 3–4 centimeters in tissue suffer from the problem of non-target exposure, because sources deposited near the periphery of the tumor will irradiate adjacent non-diseased tissues. The fourth type of isotopic radiation is the gamma ray. Much the same as X-rays, gamma rays generally traverse tissues to such an extent that most of these irradiations escape the body and they demonstrate little target to non-target selectivity resulting in widespread dosimetry problems similar to those for external beam X-ray therapy described above.

An improvement in the art would be the novel use of a radiopharmaceutical which would enhance tumor selectivity over current means, thereby allowing higher doses of radiation well in excess of generally accepted minimum effective tumor-killing doses, while at the same largely sparing radiation to normal tissues. Moreover, following the irradiation, the agent should exit the body without having exposed other critical organs, e.g. bone marrow, liver, kidneys, to dangerous levels of radioactivity. In addition, it would be desirable that the exposure of the tumor to the radioactive agent could be monitored so as to insure its proper distribution and timely removal. It would also be desirable that such candidate radiopharmaceutical should have a half-life which is long enough to allow for production and distribution to the market. The administration of the radiopharmaceutical should be accomplished with equipment available in the art, and there should be means available to trap the radiopharmaceutical as it exits the body so as to aid its disposal and minimize environmental contamination.

The following example describes the use of such a radiopharmaceutical for radiotherapy of brain tumors, but may be applicable to a number of other tumors as well. The goal is to provide a radioactive dose to the tumor which is adequate to assure a complete tumor kill, while at the same time, mining radiation burden to adjacent tissues and other radiosensitive organs. The invention consists of a novel and heretofore unappreciated method of use for the radioactive isotope Xenon-133 (Xe-133). Having been used for a number of years as a 81 KeV gamma emitting radiopharmaceutical in nuclear medicine lung scanning procedures, its utility as a diagnostic agent is well known. Xe-133 is available from nuclear reactors and has a half-life of 5.28 days which allows for its formulation, distribution and shelf life. It is generally looked on as having no utility as a therapeutic radiopharmaceutical because the penetration of its 0.346 MeV beta rays are limited to about 1 mm of tissue. Clearly, the inhalation of Xe-133 in high doses to target relatively small tumors would represent a non specific route of administration with a major total body radiation burden. The inventor has improved the art by appreciating and employing two additional dependent attributes in the use of Xe-133. First, site specific infusion of Xe-133 gas into the core of the tumor overcomes the primary disadvantage of non-specific (inhalation) delivery. However, taken lone, that would effectively limit the treatable tumor size to a few hundred milligrams because of limited tissue penetration of Xe-133 beta emissions. The invention is further enabled by the existence of Xe-133 as a gas, microbubbles of which will diffuse toward the periphery of the tumor irradiating cancerous tumor cells as they go. Near the surface of the tumor, the Xe-133 gas will encounter patent capillaries and be taken up into flowing blood and be carried to the lungs for excretion. The safety feature of diffusing Xe-133 gas being taken up into flowing capillary blood allows for very high doses to be infused, thereby assuring complete tumor kill. The inventor has conducted research which documents the presence of Xenon in the form of diffusible gas bubbles in the brain of xenon anesthetized rats. [Exhibit A]. As gas bubbles diffuse outward from the infusion site, succeeding layers of the tumor will be exposed to high fluxes of the Xe-133 beta rays at about one millimeter increments from the core to the surface of the tumor. When patent capillaries are encountered, the gas will be rapidly taken up and excreted via the lungs; hence the built-in safety feature described above. Whereas its infusion into the core and the the low tissue penetration of its beta rays helps assure the safe use of Xe-133 within the tumor, its presence as a gas assures its rapid pulmonary excretion and minimizes its stay in non-tumor tissues. The site-specific administration of Xe-133 would be accomplished through suitable small bore catheter with its tip located near the geometric center of the tumor mass, such localization being assisted by magnetic resonance imaging (MRI) and/or x-ray computer assisted tomography (CAT) scanning procedures. Ancillary equipment required for the use of the invention would include, in addition to the small bore infusion catheter, a gas-tight syringe, and a sutiable infusion pump. Such devices are available in the art. In addition, the procedure might be further simplified by tipping the infusion cathetier with the shaft of a small bore injection needle, e.g. a 30 guage insulin needle. A facilitory technique would be to thread the infusion catheter down the lumen of a somewhat more rigid guiding catheter, the latter having been advanced to the surface of the tumor. Additionally, if concurrent administration of two or more gases is desired, that could be accomplished through two or more syringe-infusion pump channels feeding into the infusion catheter through a combining manifold. Typically, the infusion catheter might be polyethylene tubing, e.g. PE10, the syringe delivery pumps would be of types supplied by Abbott, Alaris, EEC or others, and the Xe-133 infusion syringes would be of the Hamilton gas-tight variety with volumes from about 1–5 ml. Ancillary gas delivery syringe volumes would be from 1–20 ml for the administration of gases such as oxygen, helium or air as discussed below. Finally, before discussion of non-radioactive gases, it must be emphasized that Xe-133 gas represents the sole radioactive species suitable for practice of the invention, and the invention claims will be so limited.

An important adjunct in the proposed method of irradiating tumors would be the use of tissue oxygenation, since some well oxygenated tumors have been shown to be more sensitive to the effects of radaition than poorly oxygenated tumors. Tumor oxygenation could be accomplished through the same hardware described above and might be provided in advance of the Xe-133 infusion, concurrent to the Xe-133 infusion, or following the Xe-133 infusion. Such potential benefits from added oxygen will be determined through clinical experience. Moreover, it is perceived that other non-radioactive carrier gases might find use in the procedure by enhancing the Xe-133 diffusion kinetics, e.g. perhaps helium or air. Administered during or following the infusion of Xe-133, helium might be expected to speed and/or force the spread of Xe-133 throughout the tumor and thereby provide for better distribution and perhaps shorten the procedure time.

Although the use of Xe-133 infusion should be useful for all solid tumors, the most obvious initial use would be for well circumscribed inoperable brain tumors. Brain tumors are historically resisitent to chemotherapy, due, in part, to limited diffusion of chemotherapeutic drugs through the blood brain barrier. Brain tumors are also very resistant to killing via radiation, requiring over 5000 rads per gram of tumor tissue. This dose requirement effects a critical limitation in the use of external beam radiotherapy, since external beam radiation is limited by radiation ports and the non-specificity of X-irradiation. A comprehensive tumor killing dose from external X-rays, e.g. 7,000–10,000 rads per gram of tumor, might be expected to deliver a minimum of 1000 rads per gram of normal brain tissue. In practice of the invention, the Xe-133 would be contained in gas-tight syringes at doses ranging from about 10 millicuries to 250 millicuries contained in volumes from about 0.3–2.0 ml, and administered at infusion rates from about 0.01–0.2 ml per minute. Total administration times would range from about 10 minutes up to about 60 minutes, tumor diffusion times might range from less than one hour up to about seven hours, and different tumor regions might be directly exposed to Xe-133 from about 20 to 420 minutes. In the optimum use protocol, the diffusion, exposure and excretion of the radioactive Xe-133 gas would be continuously monitored by a procedure-dedicated imaging gamma camera. Upon excretion from the lungs the Xe-133 would be trapped using techniques developed for Xe-133 lung scanning procedures. In addition, one might wish to monitor the pulmonary excretion of the gas by employing a gas flow Geiger-Mueller gamma counting device to monitor the expired air.

Assuming a minimum 100% killing dose of 7,000 rads per gram of tumor, the table provided below (Table 1) lists examples of rad doses to brain tumors of increasing mass for 80 and 100 millicurie doses of Xe-133 contained in 1.0 ml of gas and infused at a rate of 0.05 ml per minute. The rate of diffusion of the gas was projected to be 0.1 gm of tumor tissue per minute.

liver, lungs, muscle, spleen, ovaries, pancreas, red marrow, bone surface, skin, testes, thymus, thyroid, urinary bladder, uterus). The total brain dose was 22.4 rads which is miniscule when comapred to the 7,000–10,000 rad dose to the tumor per se. The only other exposure would be that to the heart and lungs as the Xe-133 is excreted from the body. However, in practice, exposure from Xe-133 leaving the body could be attributed only to the 81 KeV gamma ray and would therefore be nearly equal to that from the brain, i.e. maximum of 22.4 rads. Two hour excretion kinetics would only double the exposure doses to non-target tissues. Overall, the minimum target to non-target organ irradiation ratio would be the 100 millicurie dose two-hour brain tumor versus normal brain tissue and that would be 200 (8,934/44.8 rads), a safety factor far exceeding that achievable with external beam radiotherapy.

A typical clinical use scenario for Xe-133 use in therapy of brain tumors might be as follows: The patient would be diagnosed based on clinical evidence and MRI and/or CAT scans. The determination would, in certain cases, be that the tumor is inoperable, but that Xe-133 therapy might be indicated. The procedure would include stereotactic localization of the tumor such that a guiding catheter could be advanced to the surface of the tumor. This would be accomplished following a local anesthetic to the scalp and the drilling of a burr hole (~2–3 mm in diameter) in the skull. After placement of the guiding catheter, the needle-tipped PE catheter would be advanced through the guiding catheter to the tumor surface and then forced to the tumor core, i.e. a distance equal to the radius of the tumor. This activity could be monitored with fluoroscopy. Next, the infusion catheter would be attached to the Xe-133 containing gas-tight syringe and the infusion pump started. Assuming a dead space of 0.05 ml in the catheter and an infusion rate of

TABLE 1

Rad dose for tumors of various weights resulting from radioactive emissions from Xe-133 gas diffusing from the core and filling the tumor at a rate of 0.1 gm/minute. (based on beta rays only)

| Tumor radius in cm | 0.5 | 0.75 | 1.0 | 1.25 | 1.5 | 1.75 | 2.0 |
|---|---|---|---|---|---|---|---|
| Tumor weight/volume (density taken as 1 gm/ml) | 0.5 | 1.8 | 4.2 | 8.2 | 14.1 | 22.4 | 33.5 |
| Diffusion (fill and clear) time (infusion at 0.05 ml/min for 20 min., and 0.1 gm per minute diffusion of Xe-133 throughout the tumor) | | | | | | | |
| Diffusion, in minutes | 25 | 38 | 60 | 102 | 161 | 244 | 355 |
| Tumor exposure, minutes | 25 | 33 | 44 | 60 | 79 | 103 | 131 |
| Millicuries vs Rad Dose per gram of tumor | | | | | | | |
| 100 millicuries | 57,755 | 13,468 | 12,534 | 9,695 | 9,333 | 8,904 | 8,934 |
| 80 millicuries | 46,024 | 10,766 | 10,025 | 7,756 | 7,466 | 7,123 | 7,147 |

Clearly, if a 100% effective kill radiation dose to brain tumors could be set as 7,000 rads, an 80 millicurie dose of Xe-133 would be fully sufficient, based on Table 1, to provide enough radiation for total kill of brain tumors up to about 35 grams in weight, when administered and diffusing as described above. Note, the calculation base is a MIRDOSE level (for beta rays) and equals 2.77 rads/0.1 gram per microcurie hour. For purposes of the above calculations, the dose contributed by the 81 KeV gamma ray of Xe-133 was ignored. Conversely, the dose of irradiation to non-brain tissues would totally be that contributed by the 81 KeV gamma rays. Values for other tissues from a 100 millicurie dose were examined from the MIRDOSE table and were (for a one hour tumor exposure) less than one rad for the following organs (adrenals, breasts, gall bladder wall, large intestine wall, small intestine, stomach, heart wall, kidneys, 0.05 ml per minute, radioactivity should begin to exit the tip of the needle in one minute and its appearance detected via a gamma camera. The entire infusion and disappearance of the Xe-133 isotope should be continuously monitored with a gamma camera dedicated to the procedure, i.e. up to eight hours in some cases. Initially, for kinetic balance studies, the exhalation of Xe-133 by the lungs could be monitored using a Geiger-Meuller gas flow-gamma counting system. Finally, the exhaled gases should be trapped for radioactive waste disposal. Follow-up CAT and/or MRI scans could be scheduled at suitable post treatment intervals to assess residual tumor burden and the overall efficacy of the procedure.

Monitoring of the spread of the Xe-133 gas during infusion using a gamma camera could permit an ongoing assessment of the proceedure to assure proper Xe-133 gas distribution, to aid any decision to increase or decrease the infusion rate, and/or, to initiate the admixturer of a caririer gas (e.g. helium) to accelerate diffusivity and/or excretion of Xe-133. Variables which might require such adjustments might include: 1) vascularity of the tumor; highly vascularized tumors might leak the Xe-133 at a faster rate. 2) size of the tumor; larger tumors might require higher volumes of gas. 3) tumor consistency; necrotic tumors might demonstrate resistance to flow necessitating smaller volumes and slower rates of infusion. In practice, the appropriate mix of gas volume, specific activity of the Xe-133 radionuclide and the rates of infusion would be established and perfected based on clinical experience. Whether or not to employ adjunctive oxygen infusion to sensitize the tumor cells to the effects of the Xe-133 radiation would also be established through clinical experience.

The enabling feature of this invention heretofore unappreciated in the art is the diffusional property of the Xe-133 gas microbubbles away from its nidus of adminstration. The MIRDOSE tables did not unclude diffusional considerations and it was the inventors diffusional model which permitted the dosimetry calculation estimates which provided the values in Table 1 above. This model considered that tumors would be spherical and that increasing wieights and volumes could accounted for by calculations of spheres growing by 0.5 cm diameter increments. This was required to account for the diffusional properties of the Xe-133 gas. Indeed, without the property of gaseous diffusion, the inventive use of Xenon-133 for radiotherapy of tumors would be virtually useless, and such diffusivity is dependant on the xenon gas being present in the form of gas microbubble as discovered by the inventor [Exhibit A].

Exhibit A: Abstract #481 Mar. 11, 1997: American Society for Pharmacology and Experimental Therapeutics, at San Diego, Calif. [Full article In Press—Toxicology Methods]

481

GAS MICROBUBBLE MECHANISM OF ANESTHESIA: D.R. VanDeripe, 8 Auvergne, Lake Saint Louis, Mo. 63367.

INTR: Proposed anesthetic mechanisms have favored solvated drug acting in a lipid phase in keeping with the Meyer-Overton rule. This study purports that gas and volatile anesthetics act in the form of gas microbubbles which primarily target mitocondria. METH: Rats(#), anesthetized with halothane(8), ether(5), isoflurane(3), enflurane(2), xenon(2), nitrous oxide(2), methoxyflurane(1), and pentane(1) were perfused in situ or decapitated and the brains preserved for Electron Microscopy. Untreated controls(4), and the non-anesthetics octane(1) and decane(1) were also studied. RES: Gas microbubbles, present in all cerebral cortex EM pictures were more numerous in anesthetized rats, p>0.05. EM pictures (to be shown) provide evidence that anesthetic gas bubbles block uptake of oxygen into mitochondria. DISC: Microbubbles from gasses and volatile liquids may share a common anesthetic mechanism. Differences in 37° C. vapor pressures may explain the 1.5×greater potency of i [bp 48.5° C.] over its isomer e [bp 56.5° C.] and the anesthetic activity of p [bp 36° C.] but not the more lipid soluble alkanes o [bp 125° C.] or d [bp 174° C.].

What I claim as my invention is:

1. The method of selectively infusing 10–250 millicurie doses of Xenon-133 (Xe-133) gas into the core of a tumor in a living mammal, comprising the steps:

providing a transport means comprising of a suitable length of thick-walled narrow lumen polypropylene catheter;

placing a 25–30 gauge needle on the proximal end of said transport means for tissue penetration and fluoroscopic localization at the core of the tumor;

coupling a slow rate infusion pump to the distal end of said transport means through the use of a second needle or a gas-tight connector hub;

prefilling said transport means with said Xe-133 with a specific activity of 100–200 millicuries per milliliter of Xe-133 gas;

advancing said transport means through a previously placed semi-rigid guide catheter to the tumor mass surface;

infusing said tumor with said Xe-133 gas through said transport means at a rate of 0.01–0.05 ml per minute from a 1.0–3.0 ml gas-tight syringe seated in said infusion pump; and monitoring uptake by the tumor, distribution throughout the tumor and escape of Xe-133 gas from the tumor through the use of a nuclear medicine gamma camera to permit for adjustments of infusion rates and provide for per- and post-procedural calculations of tumor dosimetry.

2. The method of claim 1 wherein said tumor is a brain tumor.

3. The method of claim 1 wherein said tumor is a prostate gland tumor.

4. The method of claim 1 wherein said tumor is a breast tumor.

5. The method of claim 1 wherein said tumor is a lung tumor.

6. The method of claim 1 wherein said tumor is a liver tumor.

7. The method of claim 1 wherein said tumor is a tumor located in the mediastinum.

8. The method of claim 1 wherein said tumor is a pancreatic tumor.

9. The method of claim 1 wherein said tumor is a ovarian tumor.

10. The method of claim 1 wherein said tumor is a tumor of the gastrointestinal tract.

11. The method of claim 1 wherein said tumor is a testicular tumor.

12. The method of claim 1 wherein said tumor is a lymph node tumor.

13. The method of claim 1 wherein said tumor is any accessible solid tumor.

14. The method of claim 1 further including the step of infusing 0.1–2.0 milliliters of oxygen prior to, during or following said infusion of said Xe-133 gas.

15. The method of claim 1 further including the step of enhancing diffusion and/or washout of said Xe-133 gas by a subsequently infusing of 1.0–10.0 milliliters of helium or air.

* * * * *